US010470975B2

United States Patent
Huysmans et al.

(10) Patent No.: US 10,470,975 B2
(45) Date of Patent: Nov. 12, 2019

(54) TAMPERPROOF ORAL DOSAGE FORM

(71) Applicant: Capsugel Belgium NV, Bornem (BE)

(72) Inventors: Tom Huysmans, Sint-Niklaas (BE); Tarryn Dierckx, Deurne (BE); Stefaan Jaak Vanquickenborne, Rijmenam (BE)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 15/769,509

(22) PCT Filed: Aug. 8, 2016

(86) PCT No.: PCT/EP2016/068840
§ 371 (c)(1),
(2) Date: Apr. 19, 2018

(87) PCT Pub. No.: WO2017/084777
PCT Pub. Date: May 26, 2017

(65) Prior Publication Data
US 2018/0303717 A1 Oct. 25, 2018

(30) Foreign Application Priority Data
Nov. 16, 2015 (EP) ..................... 15194818

(51) Int. Cl.
*A61J 3/07* (2006.01)
*C09J 103/02* (2006.01)
(Continued)

(52) U.S. Cl.
CPC .............. *A61J 3/072* (2013.01); *A61J 3/005* (2013.01); *C09J 5/00* (2013.01); *C09J 103/02* (2013.01);
(Continued)

(58) Field of Classification Search
CPC .......... A61J 3/072; A61J 3/005; C09J 103/02; C09J 105/00; C09J 5/00; C09J 2405/00;
(Continued)

(56) References Cited

U.S. PATENT DOCUMENTS 3,702,653 A 11/1972 Mottin et al.
4,539,060 A * 9/1985 Wittwer ............... A61J 3/072
156/275.1
(Continued)

FOREIGN PATENT DOCUMENTS

DE 3239955 5/1984
EP 0797424 7/2000
(Continued)

OTHER PUBLICATIONS

Extended Search Report for European Patent Application No. 15194818.9, (dated Sep. 16, 2016).
(Continued)

*Primary Examiner* — Trevor Love
(74) *Attorney, Agent, or Firm* — Klarquist Sparkman, LLP

(57) ABSTRACT

A tamperproof dosage form for oral administration comprising: a caplet comprising first and second ends, a middle region extending between said first and second ends, parallel and oppositely disposed top and bottom faces, and a land interposed between the top and bottom faces and extending along a perimeter of the caplet on a plane parallel to a caplet length axis; and first and second shells, each comprising an open end and a closed dome-shaped end, each fitted over at least a portion of the caplet, the portion comprising at least the first and/or second ends of the caplet and at least part of the middle region. An adhesive substance being arranged between the caplet and the shells at least over a portion of the top and/or bottom faces proximal to the first and second (Continued)

ends of the caplet and a corresponding portion of an inner surface of the closed dome-shaped end of the shells to fixedly join the shells to the caplet.

12 Claims, 8 Drawing Sheets

(51) Int. Cl.
| | |
|---|---|
| *A61J 3/00* | (2006.01) |
| *C09J 105/00* | (2006.01) |
| *C09J 5/00* | (2006.01) |
| *A61K 9/28* | (2006.01) |
| *A61K 9/48* | (2006.01) |
| *C08K 5/05* | (2006.01) |
| *C08L 3/02* | (2006.01) |

(52) U.S. Cl.
CPC .............. *C09J 105/00* (2013.01); *A61K 9/28* (2013.01); *A61K 9/4808* (2013.01); *C08K 5/05* (2013.01); *C08L 3/02* (2013.01); *C09J 2403/00* (2013.01); *C09J 2405/00* (2013.01)

(58) Field of Classification Search
CPC ...... C09J 2403/00; A61K 9/28; A61K 9/4808; C08K 5/05; C08L 3/02
See application file for complete search history.

(56) References Cited

U.S. PATENT DOCUMENTS

| | | | |
|---|---|---|---|
| 4,893,721 A * | 1/1990 | Bodenmann | A61J 3/071 |
| | | | 206/530 |
| 4,928,840 A | 5/1990 | Barshay et al. | |
| 5,188,688 A | 2/1993 | Boardman et al. | |
| 5,234,099 A | 8/1993 | Berta | |
| 6,126,767 A | 10/2000 | Smith et al. | |
| 2006/0286049 A1 | 12/2006 | Grethen-Pourille et al. | |
| 2007/0184077 A1* | 8/2007 | Vanquickenborne | A61J 3/072 |
| | | | 424/400 |
| 2008/0102116 A1* | 5/2008 | Perry | A61K 9/0007 |
| | | | 424/465 |
| 2009/0099265 A1 | 4/2009 | van As | |
| 2012/0045510 A1 | 2/2012 | Waldman | |
| 2016/0051479 A1 | 2/2016 | Rinker et al. | |

FOREIGN PATENT DOCUMENTS

| | | |
|---|---|---|
| EP | 3167869 | 5/2017 |
| JP | 2018535707 | 12/2018 |
| WO | WO88/01160 | 2/1988 |
| WO | WO2005/039474 | 5/2005 |

OTHER PUBLICATIONS

International Search Report and Written Opinion for PCT/EP2016/068840 (dated Apr. 20, 2017).

* cited by examiner

TAMPERPROOF ORAL DOSAGE FORM

CROSS REFERENCE TO RELATED APPLICATIONS

This is the U.S. National Stage of International Application No. PCT/EP2016/068840, filed Aug. 8. 2016, which was published in English under PCT Article 21(2), which in turn claims the benefit of European Patent Application No. 15194818.9, filed Nov. 16, 2015, which is incorporated herein in its entirety.

FIELD

The present disclosure relates to tamperproof ingestible dosage form articles suitable for the delivery of one or more medicaments or other active materials. More particularly, the dosage form articles are suitable for ingestion by a subject, preferably the subject being selected from humans or animals.

BACKGROUND

Capsule technology continues to be subject to development and improvements. In particular, over the last decades, a need for providing better tamperproofness to dosage forms has resulted in technological developments that provide some tamper resistance to such dosage forms.

For example, EP0797424B1, discloses manners by which hard capsule shells can be shrink-wrapped onto tablets to provide tightly fitted shells over the tablet. Although providing some resistance to removal of the shells, a need still exists to further improve such dosage forms to provide a truly tamper resistant product.

Other examples, like U.S. Pat. No. 6,126,767, describe manners by which shrink-wrapping of shells over tablets is combined with banding via a gelatin band or application of a gelatin dot at the apexes of the tablet over the land thereof. However, such methods result in dosage forms that have limited applications, not enabling their use in different target/controlled-release applications (whereby, for example, the use of polymeric shells are rather desirable such as pullulan, celluloses like HPMC, enteric polymers like HPMCAS, HPMCP, CAP and the like), as well as particularly suffering from tampering upon twisting of the shells (i.e. under torsion).

Other examples, such as U.S. Pat. No. 5,234,099, describe coating of tablets by dipping into a gelatinous composition to provide tamperproofness. Such methods however prove costly and may bring along with it inherent contamination issues. Moreover, such process provides some limitation as to the compositional characteristics of the gelatinous coatings that can be successfully used.

A need therefore exists for truly tamperproof dosage forms that overcome the problems of the prior art.

SUMMARY

In a first aspect of the disclosure, a tamperproof dosage form for oral administration comprising: a caplet comprising first and second ends, a middle region extending between said first and second ends, parallel and oppositely disposed top and bottom faces, and a land interposed between the top and bottom faces and extending along a perimeter of the caplet on a plane parallel to a caplet length axis; and first and second shells, each comprising an open end and a closed dome-shaped end, each fitted over at least a portion of the caplet, the portion comprising at least the first and/or second ends of the caplet and at least part of the middle region. An adhesive substance being arranged between the caplet and the shells at least over a portion of the top and/or bottom faces proximal to the first and second ends of the caplet and a corresponding portion of an inner surface of the closed dome-shaped end of the shells to fixedly join the shells to the caplet.

In a second aspect, a process of making tamperproof dosage forms.

BRIEF DESCIPTION OF THE DRAWINGS

DETAILED DESCRIPTION

Figure 1:
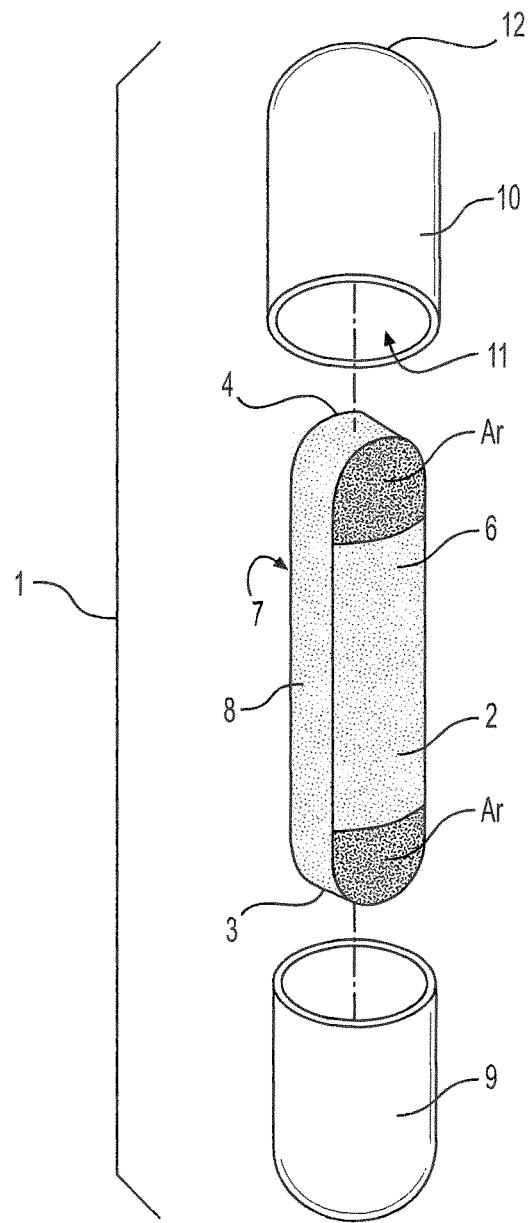
FIG. 1 is an illustration of an exploded view of a dosage form article according to one aspect of the disclosure.
Figure 2:
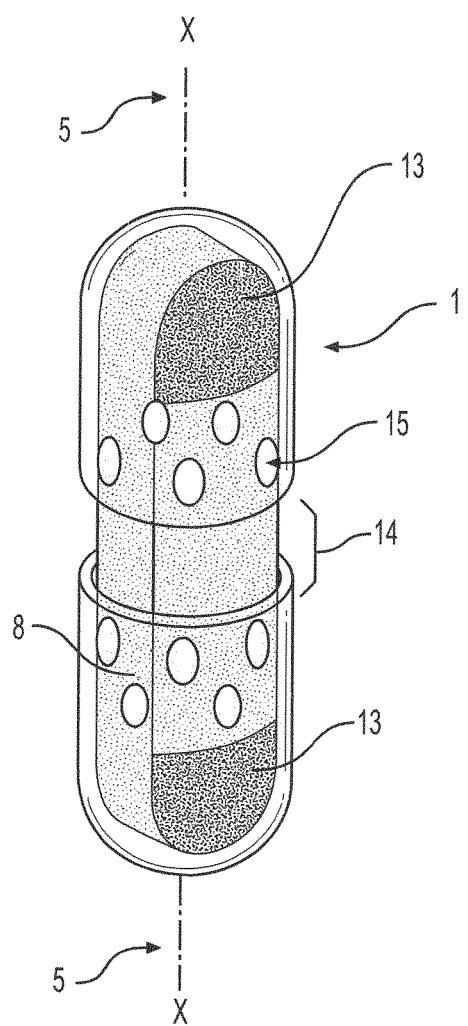
FIG. 2 is an illustration of a dosage form article according to one aspect of the disclosure.
Figure 3:
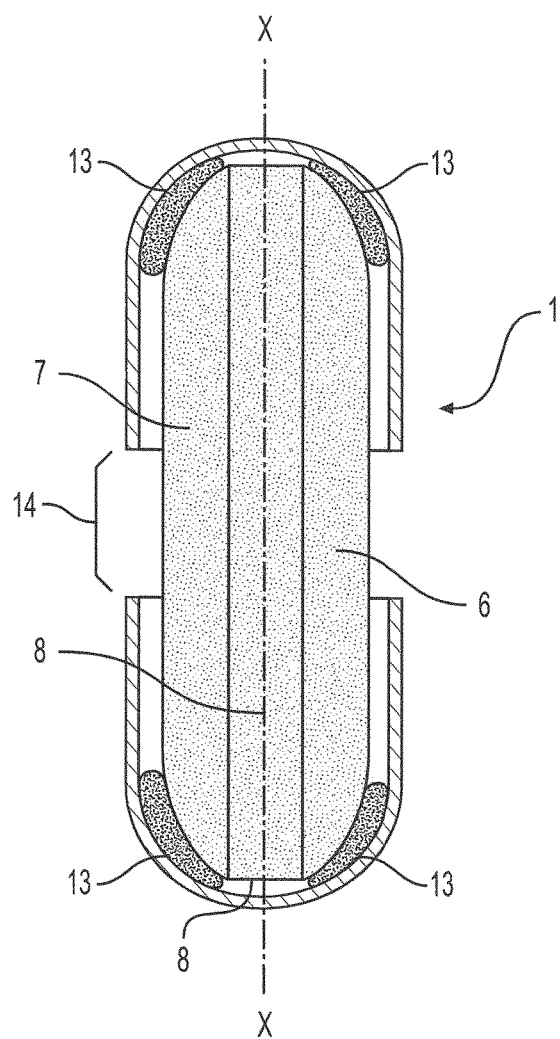
FIG. 3 is a side cross section view of FIG. 2 taken from the side (5-5) over the longitudinal axis X.
Figure 4:
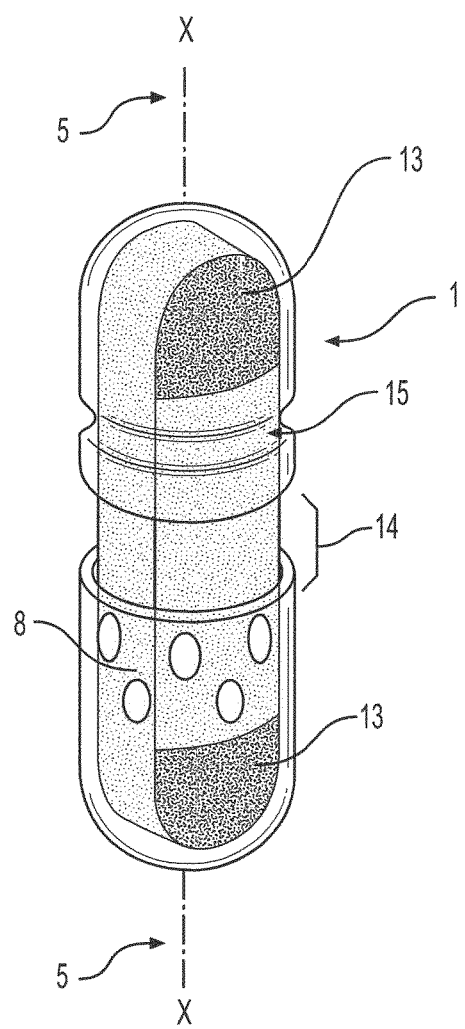
FIG. 4 is an illustration of a dosage form article according to one aspect of the disclosure.

By the term "a" and/or "an" when describing a particular element, it is intended "at least one" of that particular element.

By the term "medicament", it is intended a "drug" or the like comprising one or more compounds providing one or more curative benefits to a subject, the terms "medicament" and "drug" may be used interchangeably herein.

By the term "hard shell" or "hard capsule shell", it is intended a shell that is deformable, but which returns to its un-deformed shape upon the removal of a deforming force. Typically such shells comprise less than 25%, preferably less than 20%, more preferably from 0% to 14%, even more preferably from greater than 0% to less than 14%, water by weight.

By the term "free of organic solvent", it is intended that the level of organic solvent does not exceed 2%, preferably 1.5%, more preferably 1%, even more preferably 0.5%, even more preferably 0.2%, most preferably about 0%, by weight of the item referred to (e.g. by weight of the composition).

By the term "tamperproof" or "tamperproofness", it is intended that the opening force to separate the capsule shells from the caplet is greater or equal to the fracture strength (also commonly referred to as breaking strength or shear strength) of the caplet and/or capsule shells. Generally, the fracture strength of a dosage form may be determined by graphical analysis of a stress-strain curve following a tensile test. Typically, such opening force is greater than 15 N, preferably greater than 20 N, more preferably greater than 40 N, more preferably from 60 N to 100 N, according to the method described herein. Additionally or alternatively, such opening force may also convert to a torsion force that is greater than 100 Nmm, preferably greater than 120 Nmm, more preferably from 130 Nmm to 550 Nmm.

By the term "land or tablet/caplet/core land", it is intended the portion of the tablet (also referred to as caplet or core) that is interposed between two opposite and substantially curved faces (also referred to as top and bottom faces or surfaces) thereof. Generally the land comprises a substantially flat surface that circumscribes a perimeter of the tablet along a plane parallel to the length of the tablet and is typically a result of tablet manufacture by common tableting tools by compression. The land is also generally referred to in the art as a narrow, horizontal surface perpendicular to the tablet's periphery, which creates a junction between the tablet's periphery and the cup (also referred to a top and/or bottom face/surface of the tablet).

By the term "adhesive substance or adhesive", it is intended a substance capable of fastening two objects (or two distinct surfaces) together by molecular bonding. For example, an adhesive substance as used herein is a substance that fastens the first and/or second shells to a caplet without the need of further manipulation (such as shrinking of the shells) to attain such fastening or adhesion.

Various embodiments will now be described to provide an overall understanding of the principles of the structure, function, manufacture, and use of dosage form articles and methods disclosed herein. One or more examples of these embodiments are illustrated in the accompanying figures. Those of ordinary skill in the art will immediately understand that features described or illustrated in connection with one example embodiment can be combined with the features of other example embodiments without generalization from the present disclosure.

Dosage Form Articles

In an embodiment, a tamperproof dosage form 1 for oral administration is contemplated. The tamperproof dosage form 1 comprising: a caplet 2 comprising first and second ends 3,4, a middle region extending between said first and second ends 3,4, parallel and oppositely disposed top and bottom faces 6,7, and a land 8 interposed between said top and bottom faces 6,7 and extending along a perimeter of the caplet 2 on a plane parallel to a caplet length axis X; and first and second shells 9,10, each comprising an open end 11 and a closed dome-shaped end 12, each fitted over at least a portion of said caplet 2, said portion comprising at least said first and/or second ends 3,4 of the caplet 2 and at least part of said middle region; wherein an adhesive substance 13 is arranged between said caplet 2 and said shells 9,10 at least over a portion of the top and/or bottom faces 6,7 proximal to the first and second ends 3,4 of the caplet 2 and a corresponding portion of an inner surface of the closed dome-shaped end 12 of said shells 9,10 to fixedly join said shells 9,10 to said caplet 2. An advantage of this embodiment is that, particularly in view of the adhesive substance being present on the faces of the caplet, a greater resistance to torsion as well as tensile (or pull-apart) forces is achieved that overall results in a true tamperproof dosage form, such whilst limiting the risk of shell deformation versus collocation of the adhesive material solely at the apex of the dosage form.

Preferably, the adhesive substance is disposed over an adhesive area Ar, said adhesive area Ar corresponding to an external surface of the caplet 2 comprising at least a portion of the top and/or bottom faces 6,7 and a portion of the land 8 proximal to the first and second ends 3,4 of the caplet 2, preferably wherein said adhesive area Ar is less than the total external surface area of the caplet 2. Generally, the adhesive area Ar extends substantially continuously over the top and/or bottom faces 6,7 and the land 8. Advantageously, it has been found that it is not necessary to coat the entire caplet with adhesive substance to attain true tamperproofness thanks to the particular location of the adhesive.

In a preferred embodiment, the adhesive region Ar is greater than 5%, preferably from 10% to 35%, more preferably from 15% to 25%, of the total external surface area of the caplet 2. Adhesive regions less than 5% of the total caplet surface are ineffective in providing the desired tamperproofness, whilst adhesive regions of greater than 35% of the total caplet surface provide limited added tamperproofness and rather considerably add material cost and complexity of the process of making.

The adhesive substance 13 may be radially disposed between the caplet 2 and the first and second shells 9,10 such to substantially continuously extend parallel to the circumference of the respective shells 9,10. An advantage of this arrangement is added resistance to tampering by torsion.

In an embodiment, the adhesive substance 13 may be disposed between the caplet 2 and substantially the entire inner surface of the dome-shaped end of each first and second shells 9,10.

In a highly preferred embodiment, the first and second shells 9,10 are arranged over the caplet 2 such that a gap 14 is formed between said shells typically when the dosage form is in an assembled state. Generally, a gap 14 is formed between the first and second shells 9,10 in a direction parallel to the caplet length axis X such that at least a portion of the middle region of the caplet 2 is exposed. The presence of a gap may be beneficial for providing an aesthetic perception of added tamperproofness as well as allowing to further provide modified release (e.g. faster dissolution) of the dosage form.

In an embodiment, the outer surface of the dosage form, typically at least the outer surface of the first and second shells 9,10, comprises indicia 15 arranged to provide a tactile or visual perception of tamperproofness, preferably wherein said indicia is in the form or one or more protrusions and/or recesses. An advantage of this embodiment is to provide an added perception of tamperproofness during handling of the dosage form.

In an embodiment, the adhesive substance 13 is comprised in an amount of from 0.6% to 4%, preferably 0.12% to 2%, by weight of the caplet 2. An advantage of this embodiment is that appropriate tamperproofness is ensured without deformation of the shells that may arise at higher levels of adhesive or not be sufficient at lower levels thereof.

In an embodiment, the caplet 2 comprises one or more locking recesses and the first and/or second shells 9,10 comprise one or more locking protrusions for engagement with respective said locking recesses. An advantage of this embodiment is that further added tamperproofness is provided by combination of a mechanical locking of the shells over the caplet and the molecular adhesion of respective surfaces provided by the adhesive substance.

In an embodiment, the caplet is free of one or more subcoatings such that caplet is directly in contact with the adhesive substance. By "subcoating" it is intended herein any substance that is applied over the caplet and which has dried (e.g. is no longer in liquid form) prior to insertion of the capsule shells over the ends of the caplet, such as any prior art subcoating used to coat caplets for use in providing coated dosage forms.

In an embodiment the dosage form is not banded. An advantage of this arrangement is to retain the tamperproof benefits whilst maintaining good visual acceptance by subjects of the dosage form.

In any of the embodiments herein, the dosage form article may comprise indicia to, typically visually, or otherwise, indicate whether the dosage from has been tampered with. The indicia may be in the form of adhesive substances described herein being arranged such that it may be seen through the shells (for example by inclusion of one or more tribochromatic compounds in the adhesive substances herein as explained in more detail in the section that follows). Alternatively, or in addition, the shells may be translucent such that the indicia may be seen through the shells. The tribochromatic compounds for use herein above may be capable of changing color, preferably irreversibly, upon the application of shear. In these arrangements, the dosage form may be inspected before ingesting and provide a warning to the patient if the dosage form has been tampered.

The dosage form articles herein, preferably the shells thereof, may be made of, or consist of, an ingestible material comprising any material known in the art for making hard capsules such as gelatin (bovine, porcine or fish source), polymers (such as cellulose derivatives, polysaccharides, polyacrylates and the like). Preferably however, the material comprises one or more acid resistant and/or enteric materials, typically selected from the group consisting of hydroxypropyl methylcellulose (HPMC), cellulose acetate phthalate (CAP), hydroxypropyl methylcellulose acetate succinate (HPMCAS), hydroxypropyl methylcellulose phthalate (HP-MCP), and mixtures thereof.

Non-limiting examples of suitable shells include the following commercially available: HPMC-based capsules (such as Vcaps® or Vcaps Plus® capsules supplied by CAPSUGEL®), pullulan-based capsules (such as Plantcaps® capsules supplied by CAPSUGEL®), HPMC/Gellan gum-based capsules (such as DRcaps® capsules supplied by CAPSUGEL®), gelatin-based capsules (such as ConiSnap® capsules supplied by CAPSUGEL®), and combinations thereof.

Dosage form shells herein may be non-injection molded, and preferably made via a dip molding process. The latter ensures high production speeds and cost effectiveness. Other materials may also be used, as will be recognized by one skilled in the art, including cellulose ethers, such as starches (e.g. waxy maize starch, tapioca dextrin, and derivatives thereof), carrageenan, and polymers or copolymers of (meth)acrylic acids and derivatives thereof.

Adhesive Substance

Adhesive substances (also referred to herein as adhesive compositions) for use herein are those suitable for bonding one or more shells to a caplet to form a tamperproof dosage form for oral administration as described herein. The adhesive composition is typically an aqueous composition free of organic solvents and may comprise or consist essentially of, one or more adhesive enhancing agents and water. Typically, the adhesive substance 13 is free of gelatin.

The adhesive substance is typically in liquid form upon insertion of the shells over the caplet and typically physically and/or chemically bonds to said shells during drying which occurs generally after the shells are fully inserted over the caplet. An advantage of this arrangement is to further result in added molecular bonding achieved by the slight melting of the shell interface at the respective inner surface directly in contact with said substance. Without wishing to be bound by theory, the melted portion of the shell will dry and re-solidify together with the adhesive substance such to provide an even more evenly distributed bonding.

The adhesive composition may consist essentially of one or more adhesive enhancing agents, water and optionally an indicia imparting compound. Such is particularly desirable when the dosage form comprises indicia for indicating whether the dosage form has been tampered with.

Water is preferably comprised at a level of from greater than 25%, typically greater than 35% or even greater than 40%, preferably from 43% to 90%, preferably from 45% to 80%, more preferably from 45% to 70%, even more preferably from 45% to 60%, by weight of said composition.

The adhesive enhancing agent may be selected from the group consisting of one or more of chitosan, sugars such as sucrose, fructose, lactose, maltose, cellobiose, glucose, galactose, mannose, arabinose, sorbitol, and mixtures thereof, potato and/or corn starch, aspartame, glycosides such as steviol, synthetic homopolymers of N-vinyl-2pyrrolidone; gelatin (bovine and/or porc); monofunctional organic acid such as fatty acids, acetic acid, benzoic acid, propanoic acid, and mixtures thereof; polyfuntional organic acids such as citric acid, glycolic acid, lactic acid, mailic acid, tartaric acid, mandelic acid, fumaric acid, phosphoric acid and mixtures thereof; and mixtures thereof. Preferably the adhesive enhancing agent is selected from the group consisting of sucrose, fructose, lactose, maltose, cellobiose, glucose, galactose, mannose, arabinose, sorbitol, and mixtures thereof. Further details about suitable adhesives are provided in the following sections.

In an embodiment, the adhesive enhancing agent comprises, preferably consists essentially of, dextrose, sorbitol, mannitol, sucrose, polyvinylpyrrolidone, lactose, starch, sodium starch glycolate, hydroxypropylcellulose, ethylcellulose, maltodextrines, and mixtures theerof.

Typically, the adhesive enhancing agent is comprised at a level of from 10% to 76%, preferably from greater than 10% to 75%, preferably from 15% to 70%, more preferably from 20% to 60%, more preferably from 30% to 55%, even more preferably from 40% to 55%, by weight of the composition.

In an embodiment, the ratio of the one or more adhesive enhancing agents to water is from 0.10 to 1.30, more preferably from 0.20 to 1.00, even more preferably from 0.30 to 0.90, even more preferably from 0.60 to 0.80. Surprisingly, such ratios ensure good adhesion not only when gelatin is used as material for the dosage form shells but also when other polymer based materials are used, such as polysaccharides and celluloses as described above.

In an embodiment, the adhesive composition comprises a mixture of one or more adhesive enhancing agents, one or more film-forming agents, and one or more gliding agents. In such embodiments, the adhesive composition is preferably in liquid form during insertion of the shells over the caplet. Moreover, said composition may be further diluted with water to achieve the desired low viscosities described herein.

Film-forming agents may be selected from the group consisting of cellulosephthalateacetate, microcrystalline cellulose, methylcellulose, hydroxypropyl methylcellulose, alginates, gum arabic, carboxymethylcellulose, hydroxyethylcellulose, methylcellulose, and mixtures thereof; preferably selected from methylcellulose, hydroxypropyl methylcellulose, gum arabic, carboxymethylcellulose, hydroxyethylcellulose methylcellulose and mixtures thereof; more preferable hydroxypropyl methylcellulose.

Gliding agents may be selected from the group consisting of polyethylene glycol, polypropylene glycol, triethyl citrate, mono-, di- or triacetates of glycerol and 1,2-propyleneglycol, and mixtures thereof, preferably polypropylene glycol.

The composition may comprise a film forming agent in an amount of from 0 to about 85%, preferably from 0 to about 80%, more preferably from 0 to about 40%, even more preferably from about 5% to about 30%, most preferably from about 10% to about 25%, by weight, an adhesion enhancing agent in an amount of from about 10 to about 90%, preferably from about 35 to about 80%, more preferably from about 40 to about 70%, most preferably from about 50 to less than about 70%, by weight, and a glidant in an amount of from about 5 to about 50%, preferably about 10 to about 25, most preferably about 15 to about 20%, by weight, based on the weight of the composition.

In an embodiment, the composition may be diluted in water such to achieve the desired viscosity. The water may be contained in said composition in amounts of from 20% to 80%, preferably from 30% to 70%, more preferably from 35% to 65%, most preferably from 40% to 60%, by weight of said composition.

The adhesive composition is preferably a low viscosity and/or non-pasty adhesive composition, preferably having a viscosity of from 0.5 mPa·s to 1300 mPa·s, preferably from 0.7 mPa·s to 1200 mPa·s, more preferably from 0.9 mPa·s to 1100 mPa·s or even from 1 mPa·s to 1000 mPa·s. The viscosity generally being measured at room temperature (about 22.5° C.) with a Brookfield type LVDV II+, spindle 21, at 100 RPM.

The indicia imparting compound may be selected from one or more optional tribochromatic (i.e. tribochromic) compounds, coloring agent(s), and mixtures thereof.

Tribochromic compounds are typically colored compounds that have the property of changing color when subjected to mechanical stress, such as shear. When this compound is impregnated or applied onto a support, the color of the support will undergo a color change at the time of the mechanical stress/shear. Typical forces to be applied in order to obtain the desired tribochromic effect range from 0.01 N to 50 N, for instance from 0.1 N to 20 N, such as from 1 N to 20 N. This color change is irreversible. Once the conformation of the molecule has been modified, the latter cannot return to its initial conformation.

The color shade obtained depends on the force and the time of the mechanical stress exerted on the material. The longer and/or greater the mechanical stress, the greater the amount of tribochromic compounds whose conformation will have changed and the greater the modification of the color or the shade.

Suitable tribochromic compounds for use herein are described in paragraph 0028 to 0035 of US2006/0286049A1.

The one or more tribochromic compounds may be used alone or in combination with other colorants or pigments to provide different visual effects.

Suitable coloring agents for use herein include pharmaceutically acceptable coloring agents, food acceptable colorants, or mixtures thereof. Examples of such colorants include, but are not limited to, azo-, quinophthalone-, triphenylmethane-, xanthene- or indigoid dyes; iron oxides or hydroxides; titanium dioxide; natural dyes; and mixtures thereof. Additional examples include patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, chlorophyllin, canthaxanthin, caramel, betanin and CANDURIN® pearlescent pigments. CANDURIN® is manufactured and marketed by Merck KGaA, Darmstadt, Germany and consists of titanium dioxide and/or iron oxide (approved food and pharmaceutical colorants in many countries) and potassium aluminum silicate as a color carrier.

The indicia imparting compound may be comprised at a level of from 0% to 5%, preferably from greater than 0% to 3%, more preferably from greater than 0% to 2%, by weight of the adhesive composition.

Drug/Medicament

Dosage form articles described herein may comprise one or more drugs. Drugs suitable for use in the dosage forms described herein may take any form and be for any treatment of a human or animal subject. This includes not only pharmaceutical compounds but also dietary supplements such as vitamins, minerals and the like.

The drug may be in a state selected from solid, at room temperature and atmospheric pressure, and comprises one or more active compounds, typically in the form of a tablet (also referred to as caplet) as described herein.

Suitable compounds for delivery according to the disclosure include, but are not limited to, powder, liquid, and/or pellet forms of the following:

a) pharmaceuticals (also called pharmaceutical actives) such as betamethasone, thioctic acid, sotalol, salbutamol, norfenefrine, silymahn, dihydroergotamine, buflomedil, etofibrate, indomethacin, oxazepam, acetyldigitoxins, piroxicam, halopehdol, isosorbide mononitrate, amithptyline, diclofenac, nifedipine, verapamil, pyritinol, nitrendipine, doxycycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovirmononitrate, paracetamolol, naftidrofuryl, pentoxifylline, propafenone, acebutolol, 1-thyroxin, tramadol, bromocriptine, loperamide, ketofinen, fenoterol, cadobesilate, propranolol, minocycline, nicergoline, ambroxol, metoprolol, B-sitosterin, enalaprilhydrogenmaleate, bezafibrate, isosorbide dinitrate, gallopamil, xantinolnicotinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclopramide, acemetacin, ranitidine, biperiden, metamizol, doxepin, dipotassiumchlorazepat, tetrazepam, estramustinephosphate, terbutaline, captopril, maprotiline, prazosin, atenolol, glibenclamid, cefaclor, etilefrin, cimetidine, theophylline, hydromorphone, ibuprofen, primidone, clobazam, oxaceprol, medroxyprogesterone, flecainide, Mg-pyhdoxal-5-phosphateglutaminate, hymechromone, etofyllineclofibrate, vincamine, cinnarizine, diazepam, ketoprofen, flupentixol, molsidomine, glibornuhde, dimethindene, melperone, soquinolol, dihydrocodeine, clomethiazole, clemastine, glisoxepid, kallidinogenase, oxyfedhne, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitriptyline, caproteron, sodium valproinate, mebeverine, bisacodyl, 5-amino-salicyclic acid, dihydralazine, magaldrate, phenprocoumon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, [beta]-carotene, cloramphenicol, chlorodiazepoxid, chlormadinoneacetate, chlorothiazide, cinnarizine, clonazepam, codeine, dexamethasone, dicumarol, digoxin, drotaverine, gramicidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbital, phenylbutazone, phenytoin, prednisone, reserpine, spironolactine, streptomycin, sulfamethizole, sulfamethazine, sulfamethoxazole, sulfamethoxydiazinon, sulfathiazole, sulfisoxazole, testosterone, tolazamide, tolbutamide, trimethoprim, tyrothricin, antacids, reflux suppressants, antiflatulents, antidopaminergics, proton pump inhibitors, H2-receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, ACE inhibitors, angiotensin receptor blockers, alpha blockers, anticoagulants, heparin, antiplatelet drugs, fibrinolytic, anti-hemophilic factor, haemostatic drugs, hypolipidaemic agents, statins, hypnotics, anaesthetics, antipsychotics, antidepressants (including tricyclic antidepressants, monoamine oxidase inhibitors, lithium salts, selective serotonin reuptake inhibitors), antiemetics, anticonvulsants, antiepileptics, anxiolytics, barbiturates, movement disorder drugs, stimulants (including amphetamines), benzodiazepine, cyclopyrrolone, dopamine antagonists, antihistamines, cholinergics, anticholinergics, emetics, cannabinoids, 5-HT antagonists, analgesics, muscle relaxants, antibiotics, sulfa drugs, aminoglycosides, fluoroquinolones, bronchodilators, NSAIDs, anti-allergy drugs, antitussives, mucolytics, decongestants, corticosteroids, beta-receptor antagonists, anticholinergics, steroids, androgens, antiandrogens, gonadotropin, corticosteroids, growth hormones, insulin, antidiabetic drugs (including sulfonylurea, biguanide/metformin, and thiazolidinedione), thyroid hormones, antithyroid drugs, calcitonin, diphosphonate, vasopressin analogs, contraceptives, follicle stimulating hormone, luteinising hormone, gonadotropin release inhibitor, progestogen, dopamine agonists, oestrogen, prostaglandin, gonadorelin, clomiphene, tamoxifen, di- ethylsti 1 bestrol, antimalarials, anthelmintics, amoebicides, antivirals, antiprotozoals, vaccines, immunoglobulin, immunosuppressants, interferon, monoclonal antibodies, and mixtures thereof;

b) vitamins, e.g., fat-soluble vitamins such as vitamins A, D, E, and K, and water soluble vitamins such as vitamin C, biotin, folate, niacin, pantothenic acid, riboflavin, thiamin, vitamin B6, vitamin B12, and mixtures thereof;

c) minerals, such as calcium, chromium, copper, fluoride, iodine, iron, magnesium, manganese, molybdenum, phosphorus, potassium, selenium, sodium (including sodium chloride), zinc, and mixtures thereof;

d) dietary supplements such as herbs or other botanicals, amino acids, and substances such as enzymes, organ tissues, glandulars, and metabolites, as well as concentrates, metabolites, constituents, extracts of dietary ingredients, and mixtures thereof;

e) homoeopathic ingredients such as those listed in the Homeopathic Pharmacopoeia of the United States Revision Service (HPRS), and mixtures thereof. It must be recognized, of course, that the HPRS is periodically updated and that the present invention includes homeopathic ingredients that may be added to the HPRS; and mixtures in any combination of the foregoing.

Process of Making

The process of making tamperproof dosage forms 1 herein may comprise the steps of: providing a first shell 9 comprising an open end 11 and a closed dome-shaped end 12; applying an adhesive substance 13, preferably in liquid form, to said first shell 9 at least on an inner surface of said closed dome-shaped end 12; inserting a first end 3 of a caplet 2 through the open end 11 of said first shell 9; applying an adhesive substance 13, preferably in liquid from, to said caplet 2 on a second end 4 of the caplet 2 opposite said first end 3 and/or to a second shell 10 at least on an inner surface of said closed dome-shaped end 12; and inserting said second shell 10 over the second end 4 of said caplet 2; and optionally impacting and/or tapping said first and second shells such to further distribute the adhesive substance between said shells and said caplet; and optionally applying a drying step to allow the adhesive substance to solidify. Typically, the process steps being applied in sequence. An advantage of this process is to allow a simple and effective way of making dosage forms as described herein.

In an embodiment, the adhesive is applied on said second shell 10 whilst being held in a first orientation and the insertion of said second shell 10 over the caplet occurring in a second orientation, wherein the angle between said first and second orientations is at least 90°, preferably from 90° to 180°, preferably wherein said first orientation comprises said shell being arranged such that the centerline of said shell is parallel to an axis of gravity and said inner surface of said closed dome-shaped end holds said adhesive against the force of gravity (direction). Such arrangement has the advantage of ensuring accurate placement of the adhesive prior to insertion over the caplet.

In an embodiment, a shrinkage drying step is applied once the dosage form is in its fully assembled state, generally said step comprising reducing the moisture in the shell such to cause shrinkage thereof. Such is particularly advantageous when the shells are made of a gelatin based composition.

In an embodiment, a compression force is applied during the insertion steps at a magnitude sufficient to distribute the adhesive substance 13 throughout an interface between substantially the entire closed dome-shaped end 12 of the shells 9,10 and the caplet 2.

In an embodiment, the adhesive substance is applied radially over the inner surface of said closed dome-shaped end 12 and/or the second end 4 of the caplet 2 such that during respective insertion steps the adhesive substance is distributed over at least portion(s) of the top and/or bottom faces 6,7, preferably in the form of one or more droplets, typically as a spray. This has been found effective for appropriately locating the adhesive substance in the desired region of the dosage form.

In an embodiment, the adhesive substance is applied in the form of one or more droplets, having a diameter of from 0.1 mm to 1 mm, preferably from 0.2 mm to 0.8 mm, more preferably from 0.3 mm to 0.7 mm, more preferably from 0.4 mm to 0.7 mm.

In an embodiment the amount of adhesive substance, typically applied, is of from 0.1 mg to 15 mg, preferably from 1 mg to 10 mg, preferably from 2 mg to 9 mg, preferably from 3 mg to 8 mg, preferably from 4 mg to 7 mg, preferably from 5 mg to 6 mg. The amounts being for each shell, i.e. for two shells the above amounts being multiplied by a factor of two.

In an embodiment, the adhesive substance is applied as a spray (i.e. a plurality of droplets), preferably the spray being a conical spray (i.e. radiating outward/inward in the form of a cone). In this embodiment the spray is applied on the inner surface of the shell (and/or caplet). In this embodiment, the droplets typically have a diameter of from 10 µm to 500 µm, preferably from 10 µm to 300 µm, more preferably from 20 µm to 250 µm, even more preferably from 30 µm to 150 µm, most preferably from 40 µm to 100 µm.

In an embodiment, the process may comprise the step of providing an impacting (and/or tapping) step wherein the assembled dosage form or at least the first and/or second shells (after respective insertion steps) are tapped and/or impacted such to further distribute the adhesive substance between the caplet and the shells. Such tapping and/or impact may be provided by any suitable means arranged to tumble, drop, tap and the like, said dosage forms. Non-limiting examples include: tumbling of the assembled dosage forms in a rotating drum; vibration of the assembled dosage forms over a vibrating bed; dropping of the assembled dosage forms under the effect of gravity, such as from a transfer line at a first height to a reservoir or second transfer line at a second height thereunder; tapping, by means of an actuated tapper, the shells of the dosage form after insertion over the caplet; and combinations thereof.

EXAMPLES AND METHODS

Figure 5:
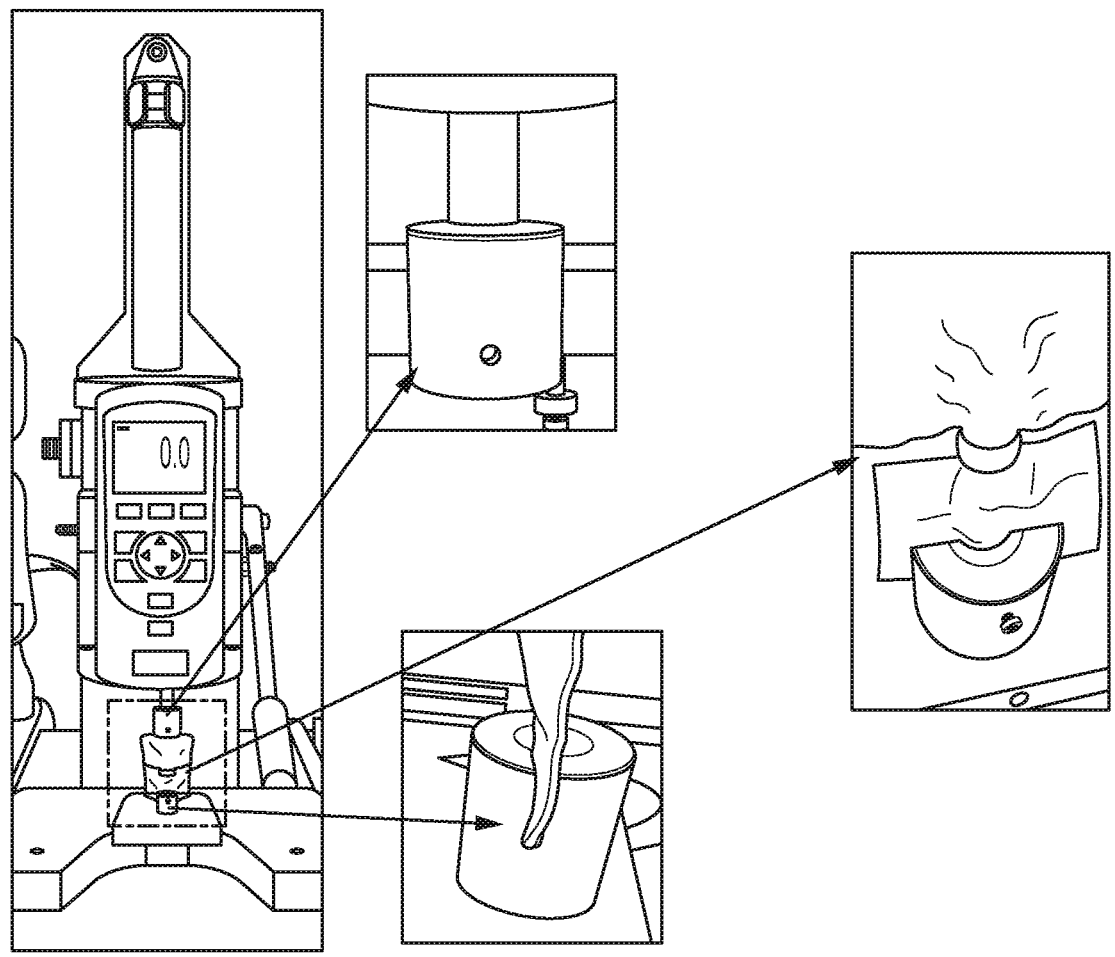
FIG. 5 is an image illustrating the set-up used to measure the pull-apart forces herein described.

Pull-Apart Test:

Pull-apart or opening forces as measured by Chatillon DFE II Series Digital Force Gauges from Ametek Inc. The test fixtures of the universal testing machine are modified to fixate the specimens without applying pressure force on them. Duct tape [3M 398FR] is first fixated separately around both shells. The outer end of the duct tape is then inserted in gauge of the test fixtures and is fixated by pressing a nail through the opening of the fixtures and tape. After correct positioning of the specimen, the peak (or ultimate) tensile strength is measured in Newtons (N). The setup is shown in FIG. 5.

Figure 6:
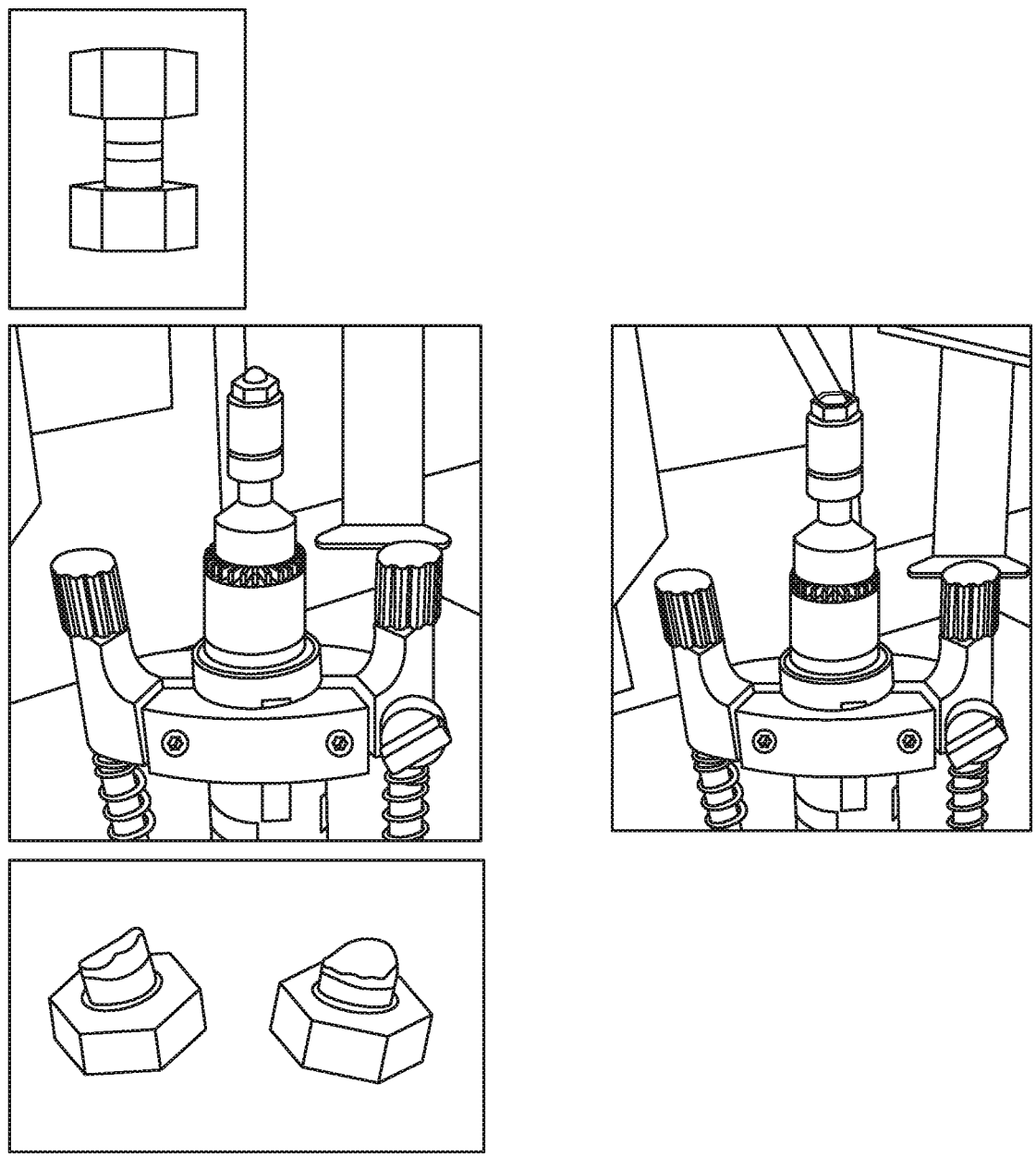
FIG. 6 is an image illustrating the set-up used to measure torsion herein described.

Torsion Test:

Torque measurements as measured by Chatillon® DFS II Series Digital force gauges with a chatillon® STS series torque sensor (TSD-50 OZ-IN) from Ametek Inc. Hex screw nuts of polyamide with minimal clearance are fixated (with cyanoacrylate glue) around (outside surface) of first and second shells. The first shell with screw nut is placed into a socket mounted on the torsion gauge. A hex screw key is then used to screw the second shell from the caplet and the torsion force recorded. The setup is shown in FIG. 6.

Example 1

Figure 7:
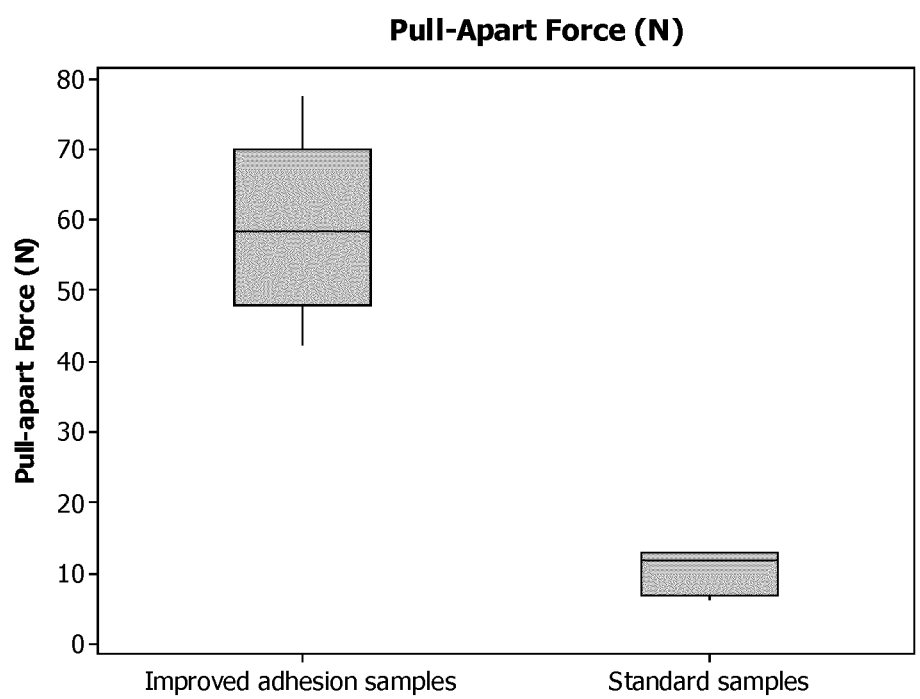
FIG. 7 is a graph showing the pull apart force of samples according to one aspect of the disclosure compared to samples of the prior art.

N=10 samples are prepared of XPress-Fit® samples with standard shells size 600 shells and Fexofenadine containing caplets (Adhesion solely due to shrinkage of shells on subcoated caplet). N=10 samples are prepared of dosage forms according to the present disclosure with standard shells size 600 shells and Fexofenadine caplets with 6 mg of adhesive (composed of 50% w/w sucrose and 50% w/w water) between shell and caplet in the cup region proximal to both ends. After compression of shells on caplet, the samples are tumbled. All samples are left at room conditions during 4 days before pull-apart tests are carried out. Results are shown in FIG. 7, the graph showing the pull-apart force variation comparing dosage forms according to the present disclosure ("improved adhesion samples") and dosage forms according to disclosure of EP0797424B1 (and sold under the name XPress-Fit® by Capsugel, "standard samples").

Example 2

Figure 8:
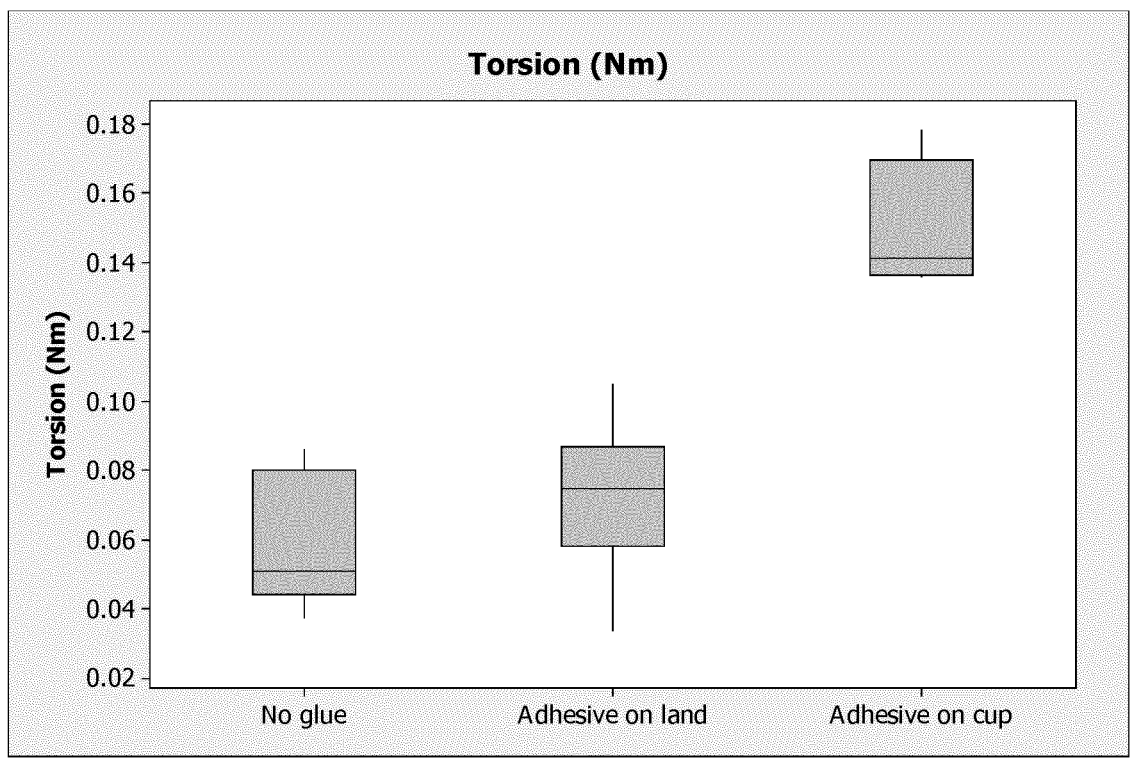
FIG. 8 is a graph showing the torsion of samples according to one aspect of the disclosure compared to samples of the prior art.

N=6 samples are prepared of XPress-Fit® samples with standard shells size 600 shells and Fexofenadine containing caplets (Adhesion solely due to shrinkage of shells on subcoated caplet). N=6 samples are prepared having shells size 600 and Fexofenadine caplets with an adhesive between shell and caplet in the land region proximal to both ends. N=6 samples are prepared of dosage forms according to the present disclosure with standard shells size 600 shells and Fexofenadine caplets with 6 mg of adhesive (composed of 50% w/w sucrose and 50% w/w water) between shell and caplet in the cup region proximal to both ends. After compression of shells on caplet, the samples are tumbled. All samples are left at room conditions during 4 days before torsion tests are carried out. Results are shown in FIG. 8.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" (i.e. every value in a practical range close to 40 mm).

The invention claimed is:

1. A tamperproof dosage form for oral administration comprising:
    a caplet comprising first and second ends, a middle region extending between said first and second ends, parallel and oppositely disposed top and bottom faces, and a land interposed between said top and bottom faces and extending completely around a perimeter of the caplet on a plane parallel to a caplet length axis (X);
    first and second shells, each comprising an open end and a closed dome-shaped end, each fitted over at least a portion of said caplet, said portion comprising at least said first and/or second ends of the caplet and at least part of said middle region;
    a gap formed between the first and second shells in a direction parallel to the caplet length axis (X) such that at least a portion of the middle region of the caplet is exposed: and
    an adhesive substance is arranged between said caplet and said shells over a portion of the top and/or bottom faces proximal to the first and second ends of the caplet and a corresponding portion of an inner surface of the closed dome-shaped end of said shells configured to join said shells to said caplet, and not on the land interposed between the top and bottom faces.

2. A tamperproof dosage form according to claim 1 wherein the adhesive area extends substantially continuously over the top and/or bottom faces.

3. A tamperproof dosage form according to claim 1 wherein the adhesive region is greater than 5% of the total external surface area of the caplet.

4. A tamperproof dosage form according to claim 1 wherein the adhesive substance comprises chitosan, sucrose, fructose, lactose, maltose, cellobiose, glucose, galactose, mannose, arabinose, sorbitol, or mixtures thereof.

5. A tamperproof dosage form according to claim 1 wherein the outer surface comprises indicia arranged to provide a tactile and/or visual perception of tamperproofness.

6. A tamperproof dosage form according to claim 1 wherein the adhesive substance is comprised in an amount of from 0.6% to 4% by weight of the caplet.

7. A tamperproof dosage form according to claim 1 wherein the caplet comprises one or more locking recesses and the first and/or second shells comprise one or more locking protrusions for engagement with respective said locking recesses.

8. A process of making a tamperproof dosage form according to claim 1 comprising the steps of:

providing a first shell comprising an open end and a closed dome-shaped end;

applying an adhesive substance to said first shell at least on an inner surface of said closed dome-shaped end;

inserting a first end of a caplet through the open end of said first shell;

applying an adhesive substance to said caplet on a second end of the caplet opposite said first end, and/or to a second shell a at least on an inner surface of said closed dome-shaped end; and inserting a second shell over the second end of said caplet.

9. A tamperproof dosage form according to claim 1 wherein the caplet is free of subcoatings such that caplet is directly in contact with the adhesive substance.

10. The tamperproof dosage form of claim 1 wherein the adhesive region (Ar) is greater than from 15% of the total external surface area of the caplet.

11. The tamperproof dosage form of claim 1 wherein the adhesive substance is free of gelatin.

12. The tamperproof dosage form of claim 5 wherein the indicia is in the form of a protrusion and/or a recess.

* * * * *